United States Patent [19]

Kopineck et al.

[11] Patent Number: 4,982,417
[45] Date of Patent: Jan. 1, 1991

[54] METHOD AND APPARATUS FOR TEXTURE ANALYSIS

[75] Inventors: Hermann J. Kopineck; Heiner Otten, both of Dortmund; Hans-Joachim Bunge, Clausthal, all of Fed. Rep. of Germany

[73] Assignee: Hoesch Stahl AG, Dortmund, Fed. Rep. of Germany

[21] Appl. No.: 386,418

[22] Filed: Jul. 27, 1989

[30] Foreign Application Priority Data

Jul. 29, 1988 [DE] Fed. Rep. of Germany ....... 3825830

[51] Int. Cl.$^5$ ............................................ G01N 23/20
[52] U.S. Cl. ........................................ 378/70; 378/72; 378/207
[58] Field of Search ................................. 378/70–72, 378/149, 54, 50, 55, 56, 207

[56] References Cited

U.S. PATENT DOCUMENTS

| | | | |
|---|---|---|---|
| 3,319,065 | 5/1967 | Webster et al. | 378/70 |
| 3,596,092 | 7/1971 | Marjorum | 378/71 |
| 3,984,679 | 10/1976 | Lublin et al. | 378/56 |
| 4,095,103 | 6/1978 | Cohen et al. | 378/72 |
| 4,125,771 | 11/1978 | Erwin | 378/72 |
| 4,633,420 | 12/1986 | Masanobu | 378/56 |
| 4,649,556 | 3/1987 | Rinik et al. | 378/71 |
| 4,715,053 | 12/1987 | Comstock et al. | 378/71 |

FOREIGN PATENT DOCUMENTS 0083841  6/1980  Japan ................................. 378/72

*Primary Examiner*—Carolyn E. Fields
*Assistant Examiner*—David P. Porte
*Attorney, Agent, or Firm*—Max Fogiel

[57] ABSTRACT

In analyzing the texture of rolled metal sheets and strips by means of X-rays or γ-rays that penetrate them, the total beam emitted by the source of radiation is divided by collimators into several component beams, and each component beam is aimed at a different angle at a component area of the sheet or strip being tested. The diffracted radiation that penetrates the sheet is analyzed in accordance with its energy distribution in detectors and the results are processed in a computer.

13 Claims, 2 Drawing Sheets

METHOD AND APPARATUS FOR TEXTURE ANALYSIS

The invention concerns a method and a device for analyzing the texture of rolled metal sheets and strips by means of X-rays or γ-rays that penetrate them and are diffracted by their crystalline structure to an extent that is analyzed and employed to calculate texture data, which are utilized to compute coefficients of texture in terms of a non-textured reference.

A method of determining a mean anisotropy $r_m$ is known from German Patent No. 2 817 742. One drawback to this method is that, every time a sample with a different texture is to be tested, the instrument must be recalibrated from a reference with that texture. Furthermore, the value $r_m$ is the only texture-related parameter that can be detected with the instrument.

Bunge and Wang, in "Computational Problems in Low Resolution Textural Analysis," on pages 163-73 of their *Theoretical Methods of Texture Analysis*, DGM Informationsgesellschaft, 1987, describe a method of determining from relatively few test results the textural coefficients needed to compute the characteristics of materials. How to obtain the results is described on page 165 of the book with particular reference to their FIG. 1. The figure illustrates a single X-ray striking a small are in the approximate shape of a point on the metal being tested. The planes of the crystal lattice that diffract the polychromatic incident X-ray are at various angles to it, and it is accordingly diffracted at a different angle at each plane. The individual resulting beams strike detectors, labeled 1 to 3 Bunge and Wang's FIG. 1. Under adequate conditions, sufficient information can be obtained with relatively few detectors from the angle of diffraction of the beams entering the detectors and from the energy distribution of the X-ray quanta or wavelengths—to calculate the textural coefficients needed to compute the material characteristics in a computer by methods described by Bunge and Wang. The appropriate conditions assumed by Bunge and Wang—that three or more detectors can be positioned in the cone of diffraction of a primary ray, occur in practice only when very thin sheets are tested. The diffraction cone is wide enough to accommodate three detectors at points that are practical for measurement purposes only when the sheet is less than 1 mm thick.

It is known that wider diffraction cones with angles of 8° or more that can accommodate several detectors can be employed only with low-energy X-rays, which cannot sufficiently penetrate thick sheets. For thicker sheets, especially those thicker than 1 mm, extremely energetic X-rays must be generated with tubes that demand more than 60 kV of operating voltage. Since diffraction angles of less than 8° must be employed with such high-energy X-rays, the cones will be extremely narrow. It is also impossible to position the detectors farther away from metal being tested to provide more space inside the cone. The detectors must be as close to the metal as possible because the intensity of the radiation decreases with the square of distance and many diffraction reflections would be below the threshold of detectable intensity if the distance were too far.

For this reason, and because after all more than one angle of incidence is also needed to test thinner sheets of metal, the Bunge and Wang method illustrated in their FIG. 1 can only rarely be employed, although their method of computer-processing the results is generally valid.

The object of the present invention is to provide a method and device employing penetrating X-rays or γ-rays whereby the textural coefficients of even thick sheets of metal can be determined extremely precisely, whereby references of known samples with different textures are tested, and whereby the measurements can be carried out even when the sheets or strips are moving.

This object is attained by the method recited in the body of claim 1 and by the device recited in the body of claim 5. Advanced embodiments of the method and device are recited in subsidiary claims 2 through 4 and 5 through 13 respectively.

Figure 1:
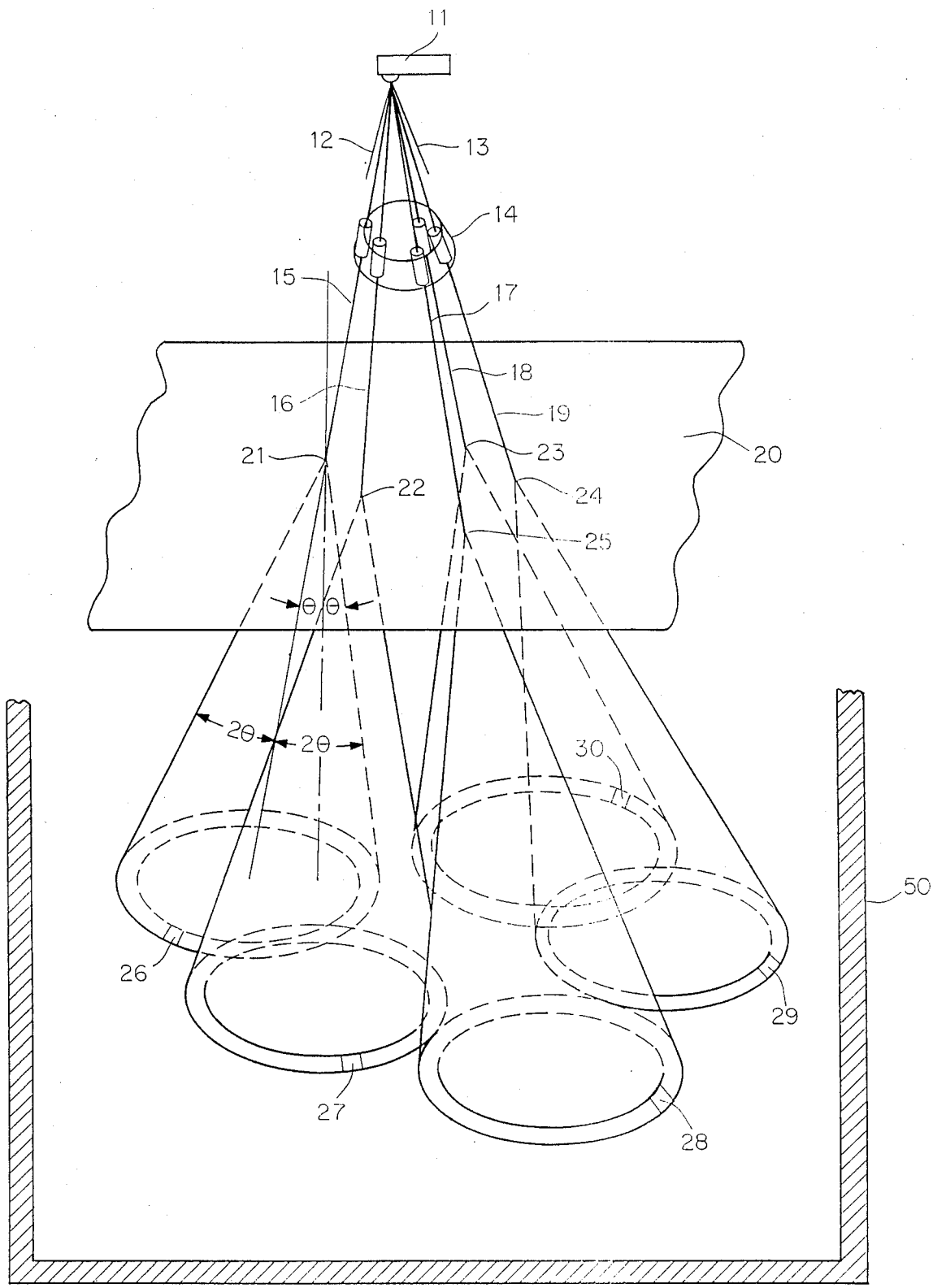
FIG. 1 illustrates the testing device.
Figure 2:
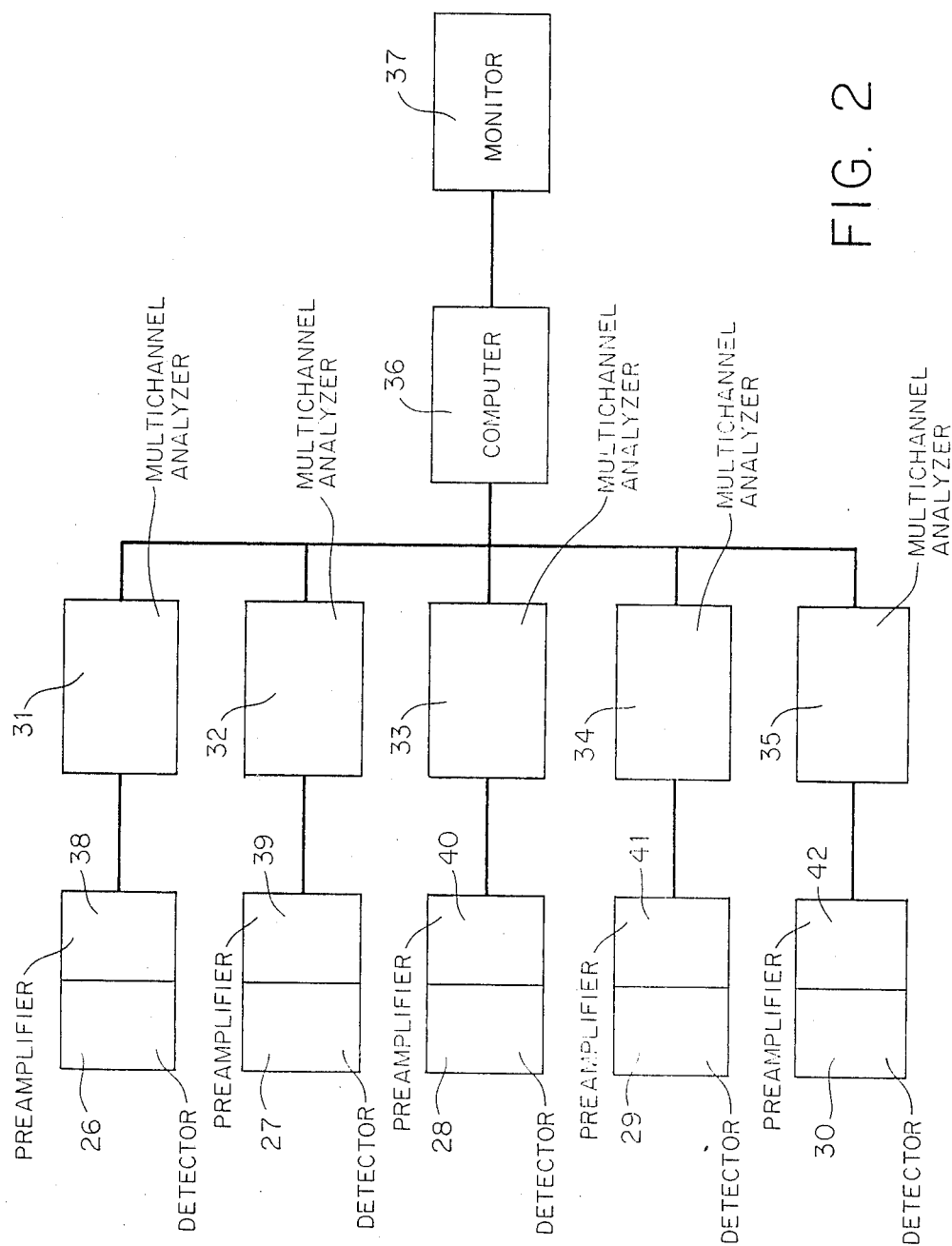
FIG. 2 is a block diagram illustrating how the results are processed.

One embodiment of the invention will now be described in detail. The X-rays leaving tube 11 are demarcated by edges 12 and 13. The radiation strikes a collimator 14 that allows through only component beams 15 to 19, which strike component areas 21 to 25 on the surface of a sheet 20 being tested. The component areas in one embodiment have a diameter of 2 mm and are all within an area that can be enclosed in an approximately 10 cm circle. The dimensions of 2 and 10 cm, rays, diffracted at sheet 20, strike detectors 26 to 30 positioned below the sheet. The diffracted rays constitute only a narrow circular ring, which is significant from the aspect of instrumentation, in the same plane as the detectors.

Although sheet 20 can be stationary, it can also be tested and evaluated while moving, at a rate of 10 to 30 m/sec through the device.

The detectors in FIG. 1 are for simplicity's sake depicted considerably smaller in relation to the ring than they actually are. Only a few points along the ring are appropriate for positioning detectors. Additional test results can be obtained by positioning another detector in the same diffraction cone.

A collimator, not illustrated in FIG. 1, is positioned in front of each detector.

The detectors 26 to 30 in the illustrated embodiment are accommodated inside a housing 50 that is chilled to approximately 190° C. with circulating helium.

Detector 26 converts the incident radiation into a voltage pulse that is amplified in a preamplifier 38. The heights of the pulses are analyzed in a multichannel analyzer 31 and assigned to specific diffraction reflections.

One preamplifier 38 to 42 and one multichannel analyzer 31 to 35 is positioned downstream of each detector 26 to 30.

Information as to the intensity of the different diffraction reflections is forwarded, sorted in accordance with each detector, to a computer 36, from multichannel pulse-height analyzers 31 to 35. The computer is programmed with the aforesaid Bunge and Wang program, allowing it to compute the textural parameters, which are displayed on a monitor 37 or printed out.

The positions of detectors 26 to 30 in the annular diffraction beams and the positions of the beams themselves in relation to one another cannot be arbitrarily established. Only points that will ensure a marked variation in intensity in response to changes in texture can be employed. To determine an anisotropy r with four detectors for example, the multichannel pulse-height analyzer must identify with satisfactory precision at least five diffraction reflections from each detector. If less than five reflections are identified, the situation can be corrected by increasing the number of detectors, which makes the device more complicated and expensive. It has been demonstrated that refections per detector can be processed with a sheet up to 4 mm thick. Although it would be possible to determine the appropriate positions by moving the detectors for example, one of skill in the art will find it practical to calculate the positions because the angle and intensity of diffractions in crystal lattices follow known laws.

In processing the test results it must be remembered that even an isotropic and assumedly untextured sheet will diffract radiation. The result is the quotient of the intensity of the reflections diffracted from the textured sample sheet or strip and those from the corresponding untextured reference.

The diffraction provoked by the planes of the crystal lattice can accordingly only be identified by the program in computer 36 once the intensity of the diffraction from the assumedly untextured sheet has been determined for the position of component areas 21 to 25. For this purpose an untextured reference is introduced into the device at the site of each component area. The computer also converts the measured results to other sheet thicknesses in accordance with known laws The untextured reference is a thin-walled flat piece of hollow plastic filled with powdered iron.

The results for the untextured reference are thoroughly corrected by testing it empty of powder to allow for the scatter intensity and absorption of the plastic by itself.

The untextured reference will need to be tested only when the first device to be manufactured is operated for the first time. When similar devices are built, the reference results obtained with the original model can be adopted. The reference can also be employed to advantage in later tests for equilibrating the device.

The method and device in accordance with the invention can be employ to advantage to determine the textures of sheets of steel. Such texture-dependent material characteristics as anisotropy, magnetic properties, and modulus of elasticity can be derived from these textures.

It is also possible to use a source of radiation with only one collimator and one beam instead of a source with several component beams produced by several collimators if the source or the collimator can be pivoted into position against a stop. The diffracted beams can accordingly be analyzed one after another as the component is pivoted in.

When Y-rays are employed instead of X-rays, five times as many component areas must be employed to determine the anisotropy, and at different angles of diffraction if necessary, because γ-rays are monochromatic and will generate only one reflection per detector. If several sources of γ-radiation with different energies are employed, the number of component areas to be irradiated can again be decreased.

Although the method in accordance with the invention can be carried out with the sources of radiation just described, the devices will be more complicated and somewhat more sensitive to malfunction.

The preferred embodiment of the invention includes, as has been thoroughly described herein, an X-ray tube and collimators to separate its beam into component beams.

In accordance with the present invention, furthermore, each of the detectors may be in the form of a single crystal. A plurality of the detectors, on the other hand, may be integrated into a chilled system of detectors. The detectors, moreover, may be positioned so that occurring predetermined positions are masked according to predetermined sheets and strips or a substantial change in intensity in relation to changes in texture.

The source or radiation has an 80 to 160 kV X-ray tube for testing sheets of steel having a thickness exceeding 2 mm. Anisotropies in sheets having a thickness exceeding 2 mm are determined at four to eight test areas, and three to seven diffraction reflections per detector are available for processing.

The detectors have positions dependent on testing results with an untextured reference. The positions of the detectors are programmed into a computer as reference values.

We claim:

1. Apparatus for testing and determining textural coefficients in rolled metal sheets and strips having a crystalline structure comprising: means for moving a sheet or strip along a predetermined path; means for aiming a plurality of beams simultaneously from a fixed source of X-rays or gamma-rays at different angles at a plurality of component areas of aid sheet or strip being tested and analyzed in terms of each component area, said X-rays or gamma-rays penetrating through the entire thickness of said sheet or strip for measuring texture through said entire thickness, said plurality of component areas being irradiated, by said beams at different angles of incidence to said component areas, said component areas comprising islands with regions between the islands being free of incident X-rays or gamma-rays; said X-rays or gamma-rays penetrating said sheet or strip and being diffracted by the crystalline structure of said sheet or strip; means for analyzing and calculating texture data dependent on crystal orientation in said crystalline structure to compute coefficients of texture in terms of a non-textured reference; means for obtaining results from said component areas and assigning said component areas to textures during further processing, and for treating the results obtained from said component areas in further processing of the results as if the results had been obtained from only one component that had been irradiated at the same angles as said plurality of component areas are irradiated at; a source of radiation for irradiating said plurality of component areas; a system of detectors positioned away from said source and inside a pencil of rays from said source; analyzers connected to processing means in the form of a computer; passage means between said source of radiation and a detector for a sheet or strip being tested; a system of collimators with apertures positioned directly in front of a window through which radiation leaves said source; at least one detector and an associated downstream analyzer for component radiation from each collimator aperture.

2. Apparatus as defined in claim 1, wherein said source of radiation comprises an X-ray tube.

3. Apparatus as defined in claim 1, wherein said source of radiation comprises gamma-radiation sources.

4. Apparatus as defined in claim 1, including analyzer means connected to a plurality of detectors, said detectors being positioned in vicinity of round annular diffraction beams.

5. Apparatus as defined in claim 1, wherein each of said detectors comprises a single crystal, a plurality of said detectors being integrated into a chilled system of detectors.

6. Apparatus as defined in claim 1, wherein said detectors are positioned so that occurring predetermined positions are masked according to predetermined sheets and strips for a substantial change in intensity in relation to changes in texture.

7. Apparatus as defined in claim 1, wherein said source of radiation has an 80 to 160 kV X-ray tube for testing sheets of steel having a thickness exceeding 2 mm.

8. Apparatus as defined in claim 1, wherein said detectors have positions dependent on test results with an untextured reference, said positions of said detectors being programmed into a computer as reference values.

9. Apparatus as defined in claim 1, wherein anisotropies in sheets having a thickness exceeding 2 mm are determined at four to eight test areas, three to seven diffraction reflections per detector being available for processing.

10. A method for analyzing texture of rolled metal sheets and strips having a crystalline structure, comprising the steps: moving a sheet or strip along a predetermined path; aiming a plurality beams simultaneously from a fixed source of X-rays or gamma-rays at different angles at a plurality of component areas of said sheet or strip being tested and analyzed in terms of each component area, said X-rays or gamma-rays penetrating through the entire thickness of said sheet or strip for measuring texture through said entire thickness, said plurality of component areas being irradiated by said beams at different angles of incidence to said component areas, said component areas comprising islands with regions between the islands being free of incident X-rays or gamma-rays; said X-rays or gamma-rays penetrating said sheet or strip and being diffracted by the crystalline structure of said sheet or strip for analyzing and calculating texture data dependent on crystal orientation in said crystalline structure to compute coefficients of texture in terms of a non-textured reference; obtaining results from said component areas and assigning said component areas to textures during further processing, and treating the results obtained from said component areas in further processing of the results as if the results had been obtained from only one component area that had been irradiated at the same angles as said plurality of component areas are irradiated at.

11. A method as defined in claim 10, wherein said sheets and strips move longitudinally while being tested and analyzed.

12. A method for analyzing texture of rolled metal sheets and strips having a crystalline structure, comprising the steps of: moving a sheet or strip along a predetermined path; aiming a plurality of beams simultaneously from a fixed source of X-rays or gamma-rays at different angles at a plurality of component areas of said sheet or strip being tested and analyzed in terms of each component area, said X-rays or gamma-rays penetrating through the entire thickness of said sheet or strip for measuring texture through said entire thickness, said plurality of component areas being irradiated by said beams at different angles of incidence to said component areas, said component areas comprising islands with regions between the islands being free of incident X-rays or gamma-rays; said X-rays or gamma-rays penetrating said sheet or strip and being diffracted by the crystalline structure of said sheet or strip for analyzing and calculating texture data dependent on crystal orientation in said crystalline structure to compute coefficients of texture in terms of a non-textured reference; obtaining results from said component areas and assigning said component areas to textures during further processing, and treating the results obtained from said component areas in further processing of the results as if the results had been obtained from only one component area that had been irradiated at the same angles as said plurality of component areas are irradiated at; and collimating radiation from one source for irradiating each component area.

13. A method as defined in claim 12, wherein three to eight component areas are irradiated when the rays are X-rays and 15 to 20 component areas are irradiated when the rays are gamma-rays.

* * * * *